US012714481B2

(12) United States Patent
Wu

(10) Patent No.: US 12,714,481 B2
(45) Date of Patent: Aug. 25, 2026

(54) BONE PLATE FOR TREATING SHOULDER JOINT INJURY

(71) Applicant: Taipei Medical University, Taipei City (TW)

(72) Inventor: Jia-Lin Wu, Taipei City (TW)

(73) Assignee: Taipei Medical University, Taipei City (TW)

(*) Notice: Subject to any disclaimer, the term of this patent is extended or adjusted under 35 U.S.C. 154(b) by 0 days.

(21) Appl. No.: 19/048,834

(22) Filed: Feb. 7, 2025

(65) Prior Publication Data

US 2026/0060728 A1 Mar. 5, 2026

(30) Foreign Application Priority Data

Sep. 2, 2024 (TW) ................................ 113133047
Sep. 2, 2024 (TW) ................................ 113209476

(51) Int. Cl.
*A61B 17/80* (2006.01)

(52) U.S. Cl.
CPC ................................ *A61B 17/8061* (2013.01)

(58) Field of Classification Search
CPC .......................... A61B 17/8061; A61B 17/809
USPC ........................................................... 606/71
See application file for complete search history.

(56) References Cited

U.S. PATENT DOCUMENTS 2,406,832 A * 9/1946 Hardinge ........... A61B 17/8009 606/71
2,486,303 A * 10/1949 Longfellow ........... A61B 17/80 606/71
3,534,731 A * 10/1970 Muller ............... A61B 17/8004 606/105
5,487,741 A * 1/1996 Maruyama ......... A61B 17/8085 606/71
5,616,142 A * 4/1997 Yuan ..................... A61F 2/2846 606/71
6,053,919 A * 4/2000 Talos ................ A61B 17/8071 606/300
8,172,842 B2 * 5/2012 Sasing .............. A61B 17/1728 606/71
8,231,625 B2 * 7/2012 Graham ............. A61B 17/8047 606/280

(Continued)

OTHER PUBLICATIONS

Cheng Xue et al., Coracoclavicular ligament attachment regions of the Chinesepopulation: a quantitative anatomic study, Anat Sci Int (2013) 88:189-194.

*Primary Examiner* — David W Bates

(57) ABSTRACT

A bone plate for treating shoulder joint injury includes a bone plate body and an aiming plate, the bone plate body includes a fixed part and a hook part. The fixed part is provided with a plurality of fixed holes and an accommodating groove thereon, the hook part is Z-shaped and is used for fixing the acromioclavicular joint, the hook part is connected to one end of the fixed part, the aiming plate is configured to be capable of being arranged in the accommodating groove of the fixed part, the aiming plate is provided with a plurality of aiming holes thereon, wherein when the fixed part is placed on the acromioclavicular joint and the aiming plate is arranged in the accommodating groove of the fixed part, the aiming hole of the aiming plate is aligned with an anatomical attachment point of an coracoclavicular ligament of the acromioclavicular joint.

8 Claims, 7 Drawing Sheets

(56) References Cited

U.S. PATENT DOCUMENTS 8,231,662 B2 * 7/2012 Huebner ............ A61B 17/8033 606/283
2002/0188296 A1 * 12/2002 Michelson ......... A61B 17/7059 606/71
2003/0074001 A1 * 4/2003 Apfelbaum ............ A61B 17/80 606/71
2003/0130661 A1 * 7/2003 Osman ............... A61B 17/7059 606/71
2003/0149434 A1 * 8/2003 Paul ................... A61B 17/7059 606/280
2003/0187440 A1 * 10/2003 Richelsoph ........ A61B 17/8042 606/295
2004/0102778 A1 * 5/2004 Huebner ............ A61B 17/8033 606/71
2007/0055251 A1 * 3/2007 Huebner ............ A61B 17/8033 606/279
2007/0123880 A1 * 5/2007 Medoff .............. A61B 17/8085 606/326
2009/0275987 A1 * 11/2009 Graham ............. A61B 17/8061 606/280
2010/0016899 A1 * 1/2010 Gelfand ............. A61B 17/0401 606/280
2010/0222779 A1 * 9/2010 Ziemek .............. A61B 17/7055 606/71
2011/0218533 A1 * 9/2011 Prandi ................ A61B 17/8004 606/71
2012/0053587 A1 * 3/2012 Kiritsis .............. A61B 17/8061 606/71
2012/0095466 A1 * 4/2012 Winslow ............ A61B 17/8061 606/71
2013/0041375 A1 * 2/2013 Fierlbeck ............. A61B 17/809 606/281
2015/0209093 A1 * 7/2015 Dallis ................ A61B 17/8061 606/281
2018/0049786 A1 * 2/2018 Brace ................. A61B 17/8047
2018/0344356 A1 * 12/2018 Zenker ............... A61B 17/8061
2021/0315659 A1 * 10/2021 Young .................... A61B 90/06
2026/0060727 A1 * 3/2026 Liang ................. A61B 17/8061

* cited by examiner prior art

BONE PLATE FOR TREATING SHOULDER JOINT INJURY

CROSS-REFERENCE TO RELATED APPLICATION

This non-provisional application claims priority under 35 U.S.C. § 119(a) on Patent Application No(s). 113133047 filed in Taiwan, R.O.C. on Sep. 2, 2024 and Patent Application No(s). 113209476 filed in Taiwan, R.O.C. on Sep. 2, 2024, the entire contents of which are hereby incorporated by reference.

BACKGROUND OF THE INVENTION

1. Field of the Invention

The present disclosure relates to a bone plate for treating shoulder joint injury, and in particular relates to a bone plate for anatomic reconstruction surgery.

2. Description of the Related Art

Acromioclavicular joint separation is a common shoulder injury disease, which often occurs in young men, and acromioclavicular joint separation accounts for about 9% of shoulder trauma. As shown in FIG. 1, the stability of the acromioclavicular joint relies primarily on the acromioclavicular ligament for horizontal stability and the coracoclavicular ligament for vertical stability. When a direct or indirect blow to the outer shoulder of the human body may cause acromioclavicular joint separation.

Severe acromioclavicular joint separation usually requires to be cured by an acromioclavicular joint surgery, if the shoulder injury occurs for less than three weeks, a bone plate fixation surgery may be performed, in which the acromial clavicle is fixed with a clavicle hook plate and then removed after four to six months; if the shoulder injury occurs for more than three weeks, the aforementioned bone plate fixation surgery is required to be combined with a coracoclavicular ligament reconstruction surgery to successfully treat the acromioclavicular joint separation. In recent years, a new type of anatomic reconstruction surgical method has been developed in coracoclavicular ligament reconstruction surgery, which refers to the anatomical position of the coracoclavicular ligament and performs ligament reconstruction by drilling holes in the clavicle.

BRIEF SUMMARY OF THE INVENTION

However, the traditional coracoclavicular ligament reconstruction surgery only knots the ligaments at the fixed end of the clavicle and then fixes the clavicle with sutures or screws. As time goes by, the aforementioned clavicle fixation position may still become loose, and thus another operation is required; if anatomical reconstruction surgery is used, the anatomical position of the coracoclavicular ligament cannot be accurately measured, making it difficult to perform anatomic reconstruction surgery. Therefore, how to reduce the difficulty of anatomical reconstruction of the coracoclavicular ligament remains a problem to be solved.

The object of the present disclosure is to provide a bone plate for treating shoulder joint injury in view of the above problem, which is applied to an acromioclavicular joint of the human body, the bone plate includes a bone plate body and an aiming plate, the bone plate body includes a fixed part, which is in the form of a long plate, the fixed part has a fixed part top surface, a fixed part bottom surface and a first end and a second end that are opposite, the fixed part is provided with a plurality of fixed holes and a hollow area thereon, the fixed holes penetrate through the fixed part top surface and the fixed part bottom surface, the hollow area is formed along a length direction of the fixed part, and the hollow area is defined with an accommodating groove; and a hook part, which is Z-shaped and is used for fixing the acromioclavicular joint, the hook part is connected to the second end of the fixed part and extends in an opposite direction of the first end and below the second end; the aiming plate is configured to be capable of being arranged in the accommodating groove of the fixed part, the aiming plate has an aiming plate top surface and an aiming plate bottom surface, the aiming plate is provided with a plurality of aiming holes thereon, the aiming holes penetrate through the aiming plate top surface and the aiming plate bottom surface, wherein when the fixed part is placed on the acromioclavicular joint and the aiming plate is arranged in the accommodating groove of the fixed part, the aiming hole of the aiming plate is aligned with an anatomical attachment point of a coracoclavicular ligament of the acromioclavicular joint.

The bone plate as described above, the accommodating groove of the fixed part is elongated, the aiming plate is configured to move linearly along the length direction of the fixed part in the accommodating groove of the fixed part.

The bone plate as described above, the fixed part bottom surface or a wall surface of the hollow area formed by the fixed part is provided with two sliding grooves thereon, the sliding grooves are communicated with a space in the accommodating groove and are respectively located on two opposite sides of the accommodating groove; the aiming plate is provided with two sliders on two opposite sides respectively, the sliders are configured to move horizontally and linearly along the length direction of the fixed part in the sliding grooves respectively.

The bone plate as described above, the sliding grooves are formed by being recessed inwards from the fixed part bottom surface, the sliders respectively protrude outward from the two opposite sides of the aiming plate.

The bone plate as described above, the sliding grooves are formed by being recessed inwards from the wall surface of the fixed part, the sliders respectively protrude outward from the two opposite sides of the aiming plate, and the sliders are blocked from moving up and down in the sliding grooves.

The bone plate as described above, the aiming plate is provided with a plurality of threading holes thereon, the threading holes penetrate through the aiming plate top surface and the aiming plate bottom surface and are located between the aiming holes.

The bone plate as described above, an arrangement direction of the threading holes on the aiming plate is not parallel to an arrangement direction of the aiming holes on the aiming plate.

In order to achieve the above object and other objects, the present disclosure provides a bone plate for treating shoulder joint injury, which is applied to an acromioclavicular joint of the human body, the bone plate includes a bone plate body and an aiming plate, the bone plate body includes a fixed part, which is in the form of a long plate, the fixed part has a fixed part top surface, a fixed part bottom surface and a first end and a second end that are opposite, the fixed part is provided with a plurality of fixed holes and a plurality of matching holes thereon, the fixed holes and the matching holes penetrate through the fixed part top surface and the fixed part bottom surface; and a hook part, which is Z-shaped and is used for fixing the acromioclavicular joint, the hook part is connected to the second end of the fixed part and extends in an opposite direction of the first end and below the second end; the aiming plate has an aiming plate top surface and an aiming plate bottom surface, the aiming plate is provided with a plurality of aiming holes thereon, the aiming holes penetrate through the aiming plate top surface and the aiming plate bottom surface, the aiming plate is configured to be capable of being arranged below the fixed part bottom surface and enabling the aiming holes to overlap with the matching holes of the fixed part, wherein when the fixed part is placed on the acromioclavicular joint and the aiming holes overlap with the matching holes of the fixed part, the aiming hole of the aiming plate is aligned with an anatomical attachment point of a coracoclavicular ligament of the acromioclavicular joint.

The bone plate as described above, the aiming plate is provided with a plurality of threading holes thereon, the threading holes penetrate through the aiming plate top surface and the aiming plate bottom surface and are located between the aiming holes, the fixed part is provided with a plurality of threading openings at the position corresponding to the threading holes, the threading openings penetrate through the fixed part top surface and the fixed part bottom surface of the fixed part; when the fixed part is placed on the acromioclavicular joint and the aiming holes overlap with the matching holes of the fixed part, the threading openings of the fixed part overlap with the threading holes of the aiming plate.

The bone plate as described above, an arrangement direction of the threading holes on the aiming plate is not parallel to an arrangement direction of the aiming holes on the aiming plate.

By using the bone plate described above, it can accurately position the anatomical attachment point of the coracoclavicular ligament during the anatomic reconstruction surgery of the coracoclavicular ligament.

DETAILED DESCRIPTION OF THE INVENTION

To fully understand the objects, features and functions of the present disclosure, details of the present disclosure are given in specific embodiments with the accompanying drawings below.

Figure 1:
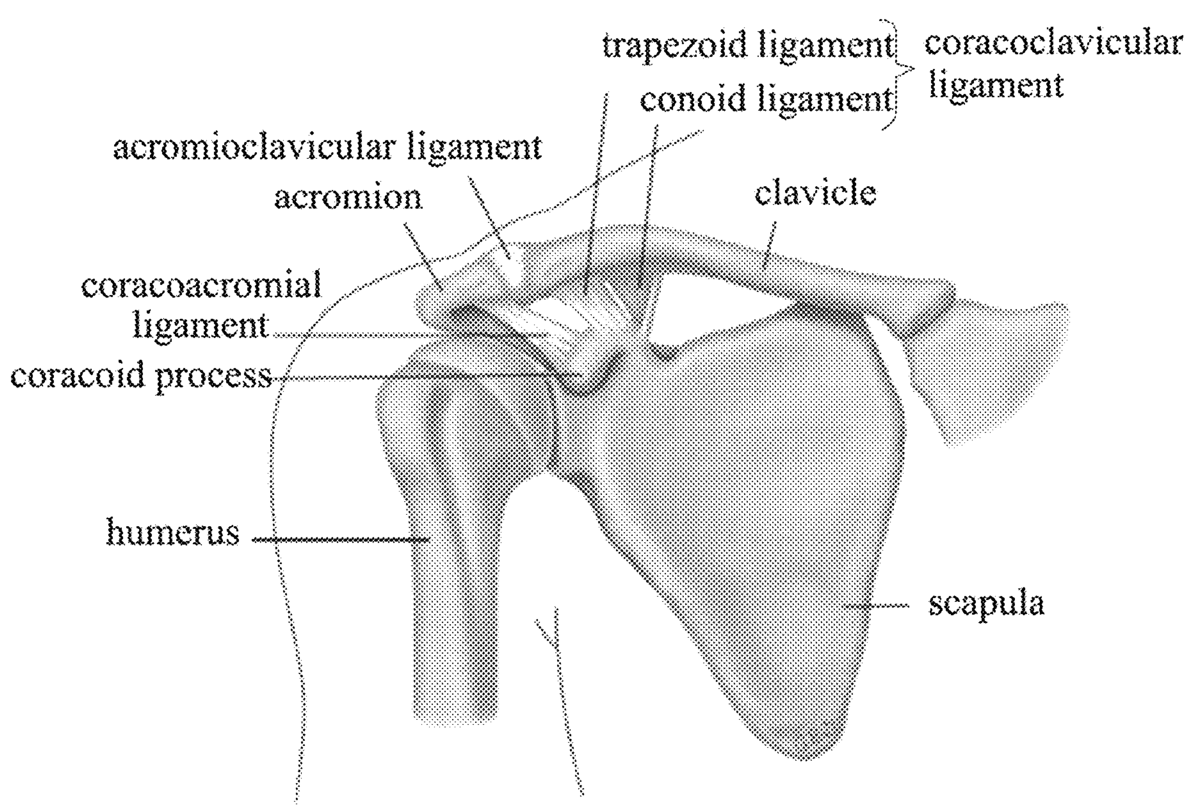
FIG. 1 is a schematic view of an anatomic structure of an acromioclavicular joint.
Figure 2:
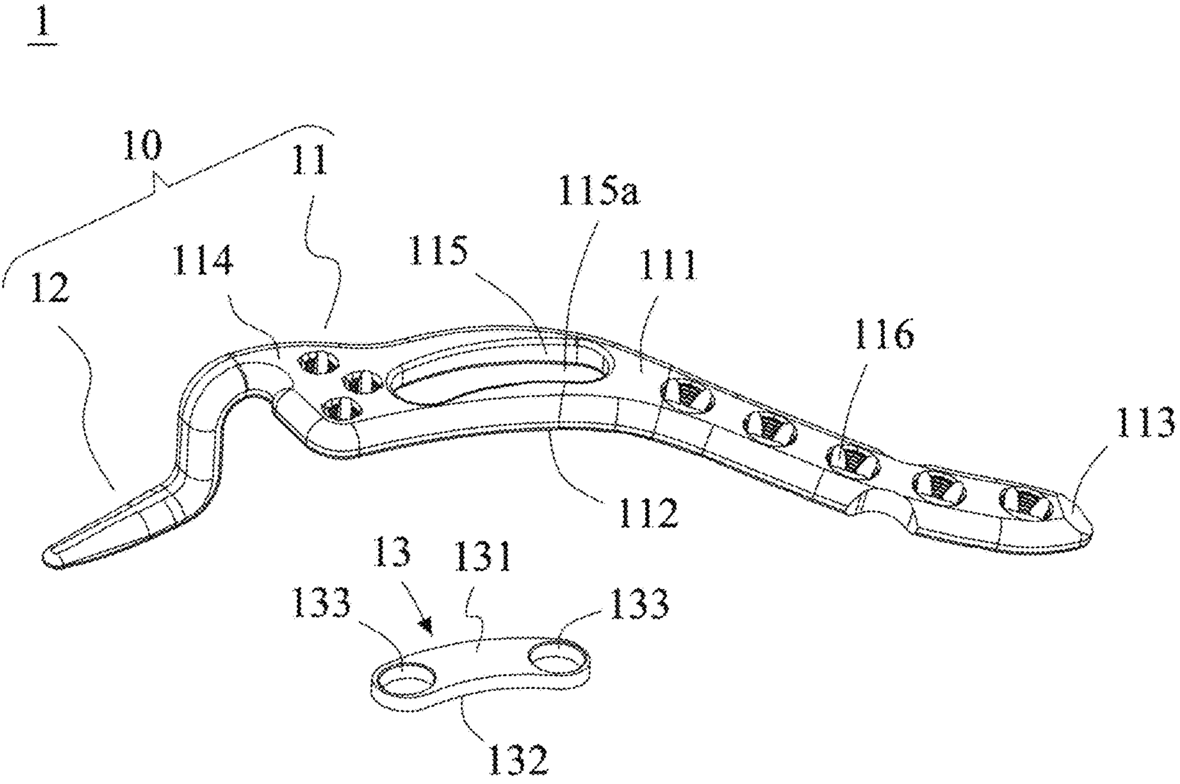
FIG. 2 is a schematic perspective view of a bone plate of embodiment 1 of the present disclosure.

Embodiment 1 of the present disclosure provides a bone plate 1 applied to an acromioclavicular joint of the human body (referring to the anatomical structure of the acromioclavicular joint in FIG. 1). Referring to FIG. 2, the bone plate 1 includes a bone plate body 10 and an aiming plate 13, and the bone plate body 10 includes a fixed part 11 and a hook part 12.

The fixed part 11 is in the form of a long plate, it has a fixed part top surface 111, a fixed part bottom surface 112 and a first end 113 and a second end 114 that are opposite, the fixed part 11 is provided with a plurality of fixed holes 116 and a hollow area 115 thereon, the fixed holes 116 penetrate through the fixed part top surface 111 and the fixed part bottom surface 112, and the hollow area 115 is formed along a length direction of the fixed part 11, and the hollow area 115 is defined with an accommodating groove **115*a***.

The hook part 12 is Z-shaped and is used for fixing the acromioclavicular joint, and the hook part 12 is connected to the second end 114 of the fixed part 11 and extends in an opposite direction of the first end 113 and below the second end 114.

The aiming plate 13 is configured to be capable of being arranged in the accommodating groove **115*a* of the fixed part 11, the aiming plate 13 has an aiming plate top surface 131 and an aiming plate bottom surface 132, the aiming plate 13 is provided with two aiming holes 133 thereon (the number of aiming holes 133 may be adjusted and increased according to the surgical demand), and the aiming holes 133 penetrate through the aiming plate top surface 131 and the aiming plate bottom surface 132**.

Figure 3:
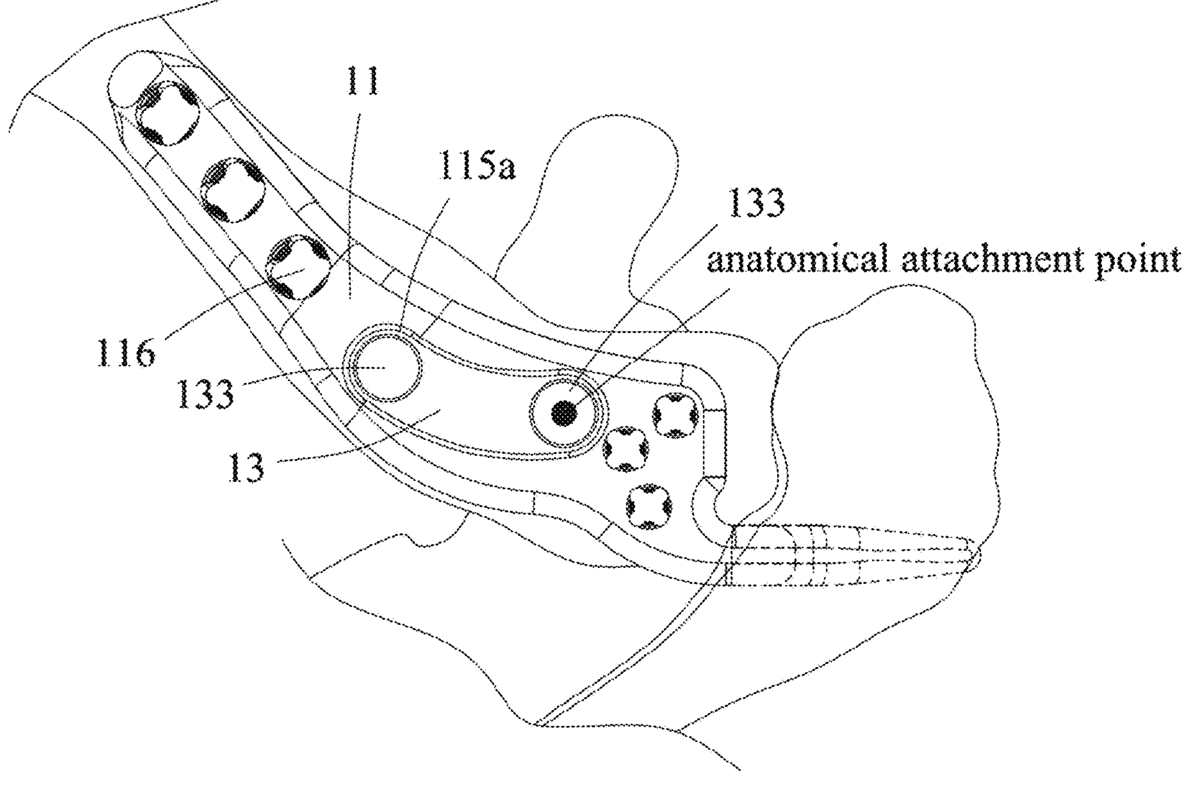
FIG. 3 is a schematic view of a placing position of the bone plate of embodiment 1 of the present disclosure in the anatomic reconstruction surgery of the coracoclavicular ligament.

The bone plate 1 is used in acromioclavicular joint surgery, and the usage is shown in FIG. 3. As shown in FIG. 3, during the operation, the bone plate 1 is placed on the acromioclavicular joint, and the hook part 12 of the bone plate 1 hooks the clavicle, so that the bone plate 1 can fix the acromioclavicular joint. The fixed holes 116 distributed on the fixed part 11 are provided for bone nails to insert into the bone. At this time, the aiming plate 13 is arranged in the accommodating groove **115*a* of the fixed part 11 (in the present embodiment 1, the aiming plate 13 is just engaged and fixed in the accommodating groove 115*a*), the position of the hollow area 115 on the fixed part 11 and the aiming holes 133 of the aiming plate 13 are designed as corresponding to anatomical attachment points of the coracoclavicular ligament of the acromioclavicular joint of the human body (the design of the anatomical attachment point refers the anatomical data of Asians disclosed in the literature, literature source: Xue. C et al. Anat Sci Int, 2013)), since the two aiming holes 133** correspond precisely to the two anatomical attachment points on the coracoclavicular ligament, the surgeon can perform anatomic reconstruction surgery of the coracoclavicular ligament based on the two anatomical attachment points.

Through the above-mentioned bone plate 1, the surgeon can accurately position the anatomical attachment point of the coracoclavicular ligament in the anatomic reconstruction surgery of the coracoclavicular ligament, and then solve the problem that the anatomical position of the coracoclavicular ligament cannot be accurately measured, which makes it difficult to perform anatomic reconstruction surgery.

On the other hand, as mentioned above, the bone plate will be removed four to six months after the coracoclavicular ligament reconstruction surgery, the clavicle fixing position may still loosen over time, and since the aiming plate 13 is detachably placed in the accommodating groove **115*a* of the fixed part 11, when removing the bone plate 1, the surgeon only needs to remove the fixed part 11 of the bone plate 1, that is, the main body of the bone plate 1, and the aiming plate 13 still remains in the coracoid clavicle, the aiming plate 13** has the effect of strengthening the mechanical strength of the coracoid clavicle at this time, so as to avoid the loosening of the clavicle fixing position of or the occurrence of fracture again after surgery.

Figure 4:
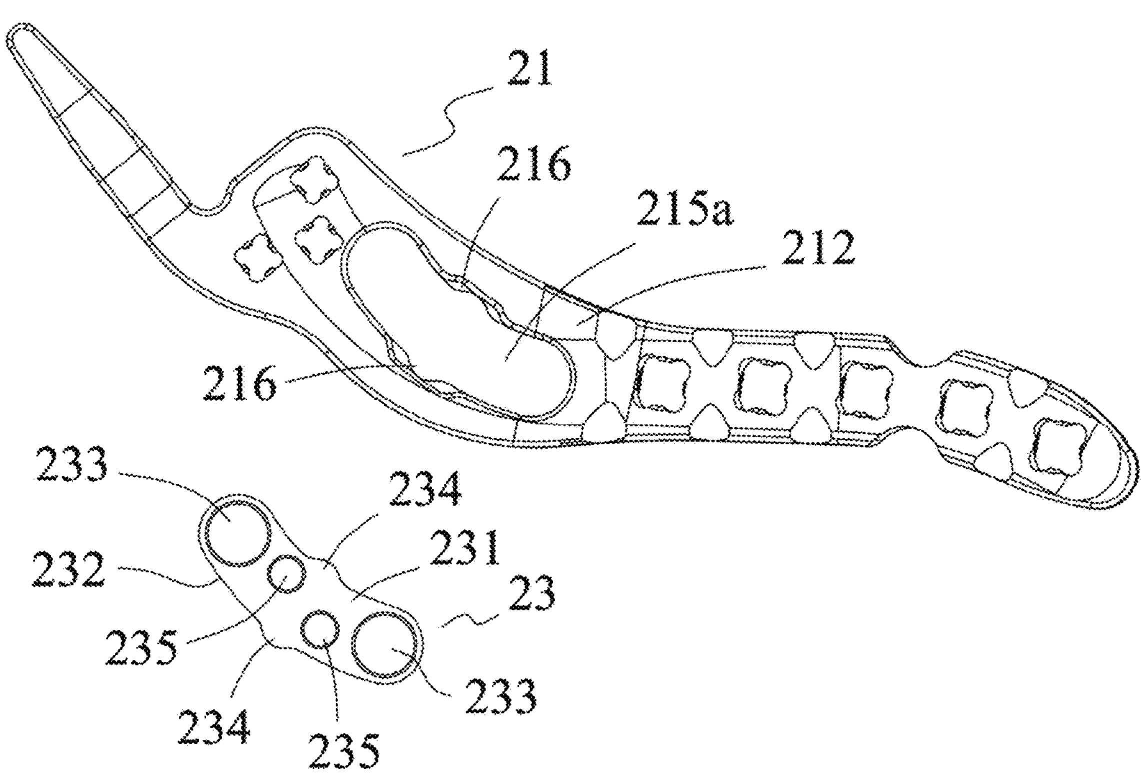
FIG. 4 is a schematic perspective view of a bone plate of embodiment 2 of the present disclosure.

Embodiment 2 of the present disclosure provides a bone plate 2, referring to FIG. 4, the main structure and function of the bone plate 2 of the present embodiment 2 and the bone plate 1 in embodiment 1 are roughly the same, the main difference is that the bone plate 2 is designed to enable the aiming plate 23 to move linearly along the length direction of the fixed part 21 in an accommodating groove 215*a* of the fixed part 21. Different patients may have different individual's anatomical attachment points due to differences in their bone structures, the above design allows the aiming plate 23 to adjust the positions of the two aiming holes 233, and accurately displace and adjust the aiming holes 233 to target anatomical attachment points according to the positions of anatomical attachment points required by the individual's actual surgery.

Figure 5:
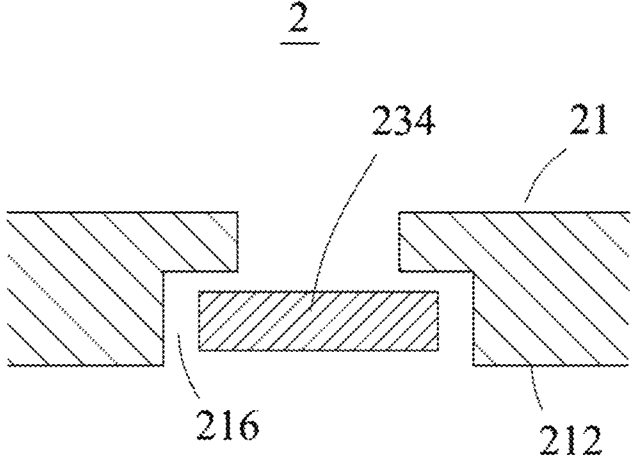
FIG. 5 is a schematic partial sectional view of the bone plate of embodiment 2 of the present disclosure.

The specific structural design also refers to FIGS. 4 and 5. The accommodating groove 215*a* is elongated, the fixed part bottom surface 212 is provided with two sliding grooves 216 thereon, the sliding grooves 216 are communicated with a space in the accommodating groove 215*a* and are respectively located on two opposite sides of the accommodating groove 215*a*, and the sliding grooves 216 are formed by being recessed inwards from the fixed part bottom surface 212. The aiming plate 23 is provided with two sliders 234 on two opposite sides respectively, the sliders 234 respectively protrude outward from the two opposite sides of the aiming plate 23, and the sliders 234 are configured to move horizontally and linearly along the length direction of the fixed part 21 in the sliding grooves 216 respectively, that is, move on the clavicle along the length direction of the clavicle, so that the aiming plate 23 is adjusted to the target anatomical attachment points. In addition, because the sliding grooves 216 are formed by being recessed inwards from the fixed part bottom surface 212, the slider 234 of the aiming plate 23 is against the inner wall forming the sliding groove 216 during the sliding process, so that the upward displacement of the slider 234 of the aiming plate 23 in the sliding process can be limited, and the aiming plate 23 is prevented from being disengaged from the fixed part 21.

In addition, the aiming plate 23 is further provided with two threading holes 235 thereon (the number of threading holes 235 may be adjusted and increased according to the surgical demand), and the threading holes 235 penetrate through the aiming plate top surface 231 and the aiming plate bottom surface 232 of the aiming plate 23 and are located between the two aiming holes 233. The threading holes 235 are used for non-absorbable threads (e.g. fibers of special composition) to be threaded for internal brace, which is to suture the aforesaid thread with the coracoclavicular ligament to enhance the fixature of the coracoclavicular ligament, and improve the success rate of coracoclavicular ligament reconstruction surgery. However, in other aspects, the aiming plate 23 may not be designed with threading holes thereon according to the using demand, and is not limited to the present embodiment 2.

In the present embodiment 2, the threading holes 235 are designed such that an arrangement direction on the aiming plate 23 is not parallel to an arrangement direction of the aiming holes 233 on the aiming plate 23, so that after the operation, a fixing structure established on the threading holes 235 and the binding structures on the aiming holes 233 are staggered in fixed directions, thereby enhancing the overall structural strength of the coracoclavicular ligament reconstruction structure. However, the arrangement direction of the threading holes 235 may still be adjusted arbitrarily according to other requirements, and is not limited to the present embodiment 2.

Figure 6:
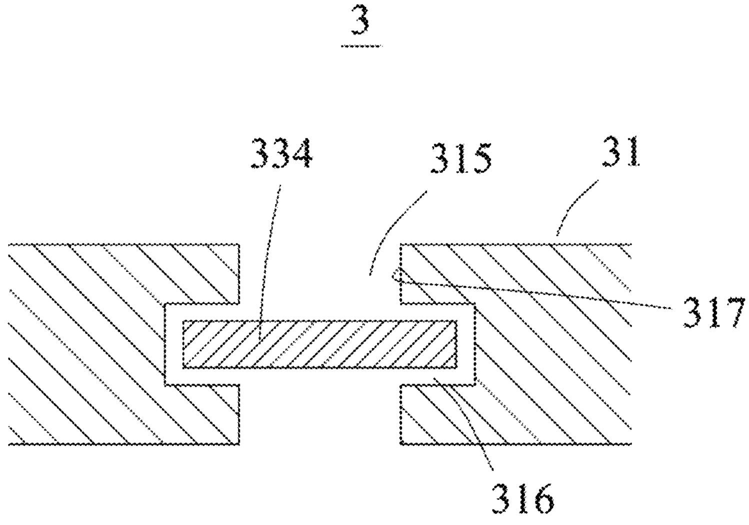
FIG. 6 is a schematic partial sectional view of a bone plate of embodiment 3 of the present disclosure.

Embodiment 3 of the present disclosure provides a bone plate 3, referring to FIG. 6, the main structure and function of the bone plate 2 in the present embodiment 3 and the bone plate 2 in embodiment 2 are roughly the same, the main difference is that the two sliding grooves 316 of the bone plate 3 are arranged on a wall surface 317 of the fixed part 31 of the bone plate 3 which forms a hollow area 315, and the sliding grooves 316 are recessed inwards from the wall surface 317 of the fixed part 31 and forms a concave shape, the two sliders 334 of the bone plate 3 are configured to be able to move horizontally and linearly along the length direction of the fixed part 31 respectively in the sliding grooves 316, and the sliders 334 are blocked from moving up and down in the sliding grooves 316 formed in a concave shape, so that the up and down displacement of the sliders 334 in the sliding process can be limited and the aiming plate (not shown in FIG. 6) is prevented from disengaging from the fixed part 31.

Figure 7:
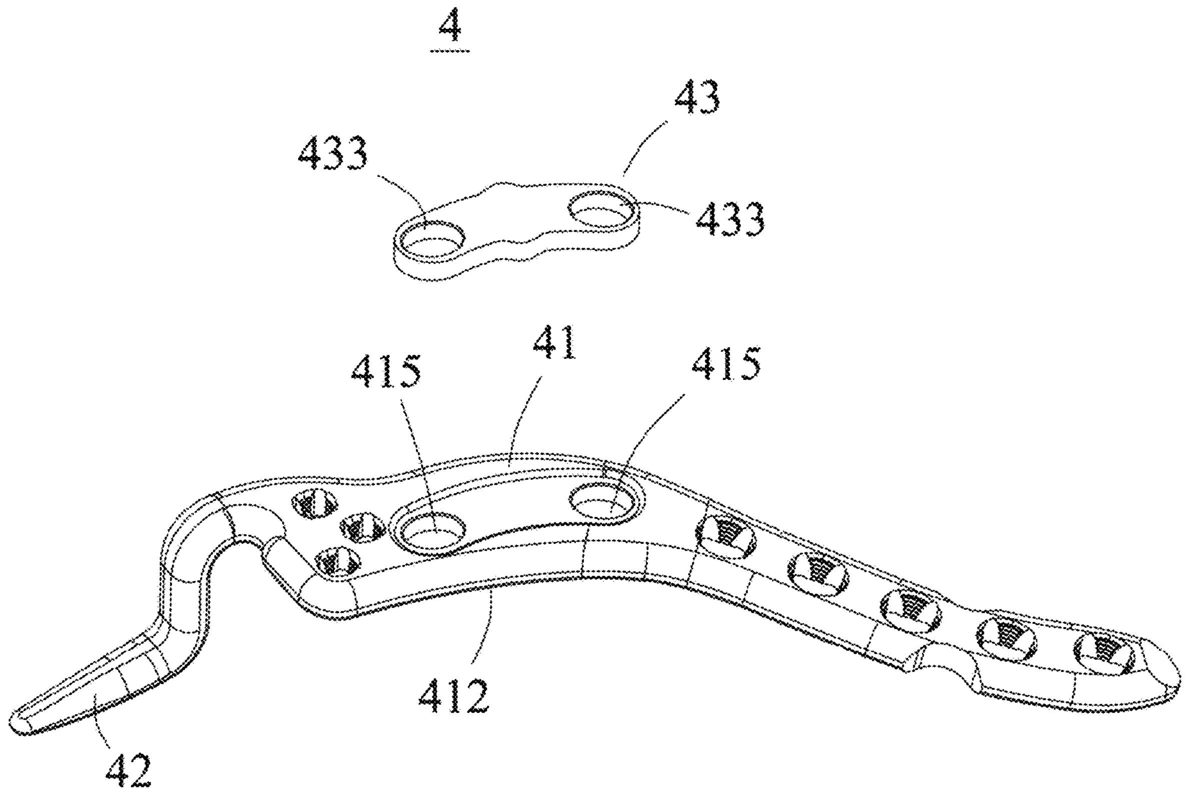
FIG. 7 is a schematic perspective view of a bone plate of embodiment 4 of the present disclosure.

Embodiment 4 of the present disclosure provides a bone plate 4, referring to FIG. 7, the main structure and function of the bone plate 4 of the present embodiment 4 and the bone plate 2 in embodiment 2 are roughly the same, the main difference is that the fixed part 41 of the bone plate 4 is not designed with a hollow area, and the original position is changed to be designed with two matching holes 415 corresponding to the two aiming holes 433 of the aiming plate 43 of the bone plate 4, the aiming plate 43 is configured to be capable of being arranged below the fixed part bottom surface 412 of the fixed part 41 and enabling the aiming holes 433 to overlap with the matching holes 415 of the fixed part 41, and during the operation, when the fixed part 41 is placed on the acromioclavicular joint, the aiming holes 433 overlap with the matching holes 415 of the fixed part 41, and the aiming hole 433 of the aiming plate 43 is aligned with the anatomical attachment point of the coracoclavicular ligament of the acromioclavicular joint, the aiming holes 433 together with the matching holes 415 form a surgical channel. The bone plate 4 replaces the design of the hollow area through the matching holes 415, so that the surgeon can also use the bone plate 4 to accurately position the anatomical attachment points of the coracoclavicular ligament in the anatomical reconstruction surgery of the coracoclavicular ligament, and the fixed part 41 of the bone plate 4 simplifies the processing process of the bone plate and reduces the processing cost because it does not need to be hollowed out.

Figure 8:
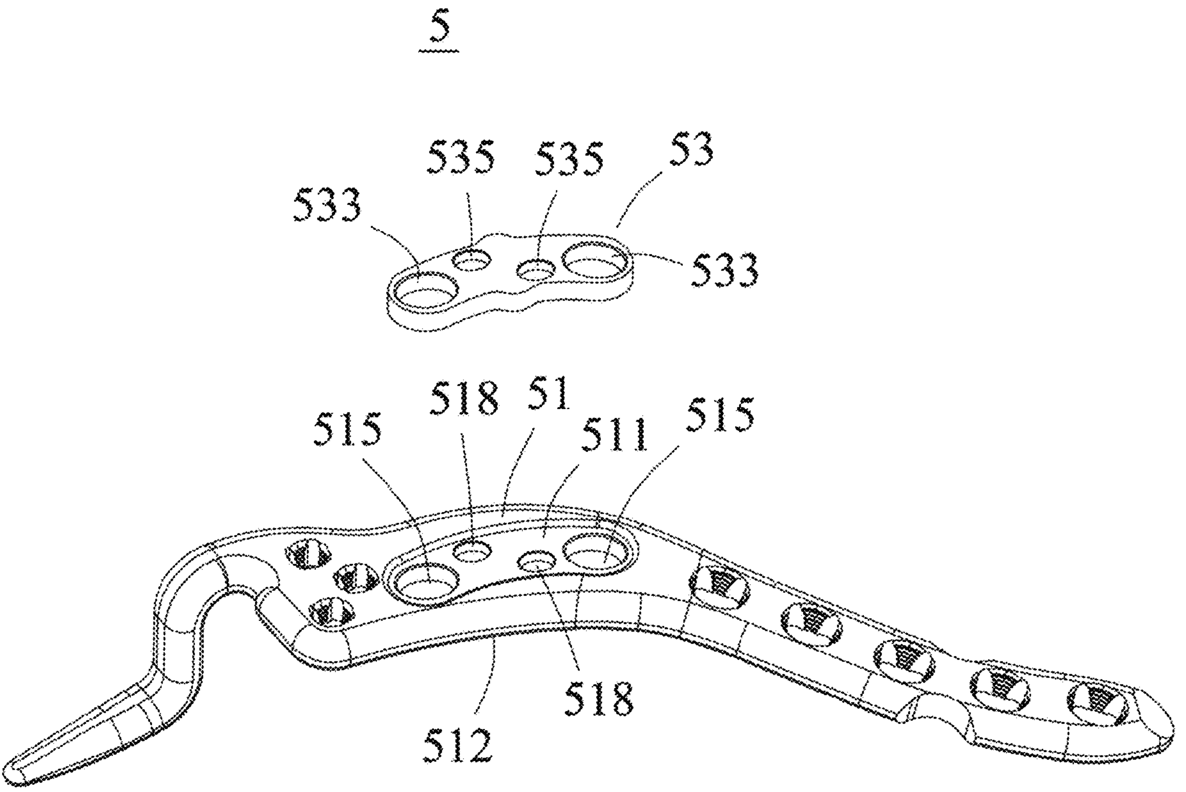
FIG. 8 is a schematic perspective view of a bone plate of embodiment 5 of the present disclosure.

Embodiment 5 of the present disclosure provides a bone plate 5, referring to FIG. 8, the main structure and function of the bone plate 5 of the present embodiment 5 and the bone plate 4 in embodiment 4 are roughly the same, the main difference is that two threading holes 535 are further arranged on an aiming plate 53 of the bone plate 5, the function and structure of the threading holes 535 are the same as the threading holes 235 in the above embodiment 2, and a fixed part 51 of the bone plate 5 is also provided with two threading openings 518 at the position corresponding to the threading holes 535, the threading openings 518 penetrate through a fixed part top surface 511 and a fixed part bottom surface 512 of the fixed part 51. When the aiming plate 53 is arranged below the fixed part bottom surface 512 of the fixed part 51 and two aiming holes 533 of the aiming plate 53 overlap with two matching holes 515 of the fixed part 51, the threading openings 518 also overlap with the threading holes 535, so that the aforesaid non-absorbable threads can be first threaded into the two threading openings 518 of the fixed part 51 and then pass through the two threading holes 535 of the aiming plate 53, so as to carry out the aforesaid internal brace.

Although various embodiments have been described for illustrative purposes, it is obvious to those skilled in the art that various alterations and improvements can be made without departing from the spirit and scope of the present invention as defined in the claims as attached.

What is claimed is:

1. A bone plate for treating shoulder joint injury, configured to be applied to an acromioclavicular joint of the human body, the bone plate comprising:

a bone plate body, comprising:

a fixed part, being in the form of a long plate, the fixed part has a fixed part top surface, a fixed part bottom surface and a first end and a second end that are opposite, the fixed part is provided with a plurality of fixed holes and a hollow area thereon, the fixed holes penetrate through the fixed part top surface and the fixed part bottom surface, and the hollow area is formed along a length direction of the fixed part, the hollow area is defined with an accommodating groove; and a hook part, being Z-shaped and used for fixing the acromioclavicular joint, the hook part is connected to the second end of the fixed part and extends in an opposite direction of the first end and below the second end; and an aiming plate, configured to be capable of being arranged in the accommodating groove of the fixed part, the aiming plate has an aiming plate top surface and an aiming plate bottom surface, the aiming plate is provided with a plurality of aiming holes thereon, the aiming holes penetrate through the aiming plate top surface and the aiming plate bottom surface, wherein when the fixed part is placed on the acromioclavicular joint and the aiming plate is arranged in the accommodating groove of the fixed part, the aiming hole of the aiming plate is aligned with an anatomical attachment point of a coracoclavicular ligament of the acromioclavicular joint, wherein the aiming plate is provided with a plurality of threading holes thereon, the threading holes penetrate through the aiming plate top surface and the aiming plate bottom surface and are located between the aiming holes, and an arrangement direction of the threading holes on the aiming plate is not parallel to an arrangement direction of the aiming holes on the aiming plate.

2. The bone plate according to claim 1, wherein the accommodating groove of the fixed part is elongated, the aiming plate is configured to move linearly along the length direction of the fixed part in the accommodating groove of the fixed part.

3. The bone plate according to claim 2, wherein the fixed part bottom surface or a wall surface of the hollow area formed by the fixed part is provided with two sliding grooves thereon, the sliding grooves are communicated with a space in the accommodating groove and are respectively located on two opposite sides of the accommodating groove; the aiming plate is provided with two sliders on two opposite sides respectively, the sliders are configured to move horizontally and linearly along the length direction of the fixed part in the sliding grooves respectively.

4. The bone plate according to claim 3, wherein the sliding grooves are formed by being recessed inwards from the fixed part bottom surface, the sliders respectively protrude outward from the two opposite sides of the aiming plate.

5. The bone plate according to claim 3, wherein the sliding grooves are formed by being recessed inwards from the wall surface of the fixed part, the sliders respectively protrude outward from the two opposite sides of the aiming plate, and the sliders are blocked from moving up and down in the sliding grooves.

6. A bone plate for treating shoulder joint injury, configured to be applied to an acromioclavicular joint of the human body, the bone plate comprising:

a bone plate body, comprising:

a fixed part, being in the form of a long plate, the fixed part has a fixed part top surface, a fixed part bottom surface and a first end and a second end that are opposite, the fixed part is provided with a plurality of fixed holes and a plurality of matching holes thereon, the fixed holes and the matching holes penetrate through the fixed part top surface and the fixed part bottom surface; and a hook part, being Z-shaped and used for fixing the acromioclavicular joint, the hook part is connected to the second end of the fixed part and extends in an opposite direction of the first end and below the second end; and an aiming plate, having an aiming plate top surface and an aiming plate bottom surface, the aiming plate is provided with a plurality of aiming holes thereon, the aiming holes penetrate through the aiming plate top surface and the aiming plate bottom surface, the aiming plate is configured to be capable of being arranged below the fixed part bottom surface and enabling the aiming holes to overlap with the matching holes of the fixed part, wherein when the fixed part is placed on the acromioclavicular joint and the aiming holes overlap with the matching holes of the fixed part, the aiming hole of the aiming plate is aligned with an anatomical attachment point of a coracoclavicular ligament of the acromioclavicular joint.

7. The bone plate according to claim 6, wherein the aiming plate is provided with a plurality of threading holes thereon, the threading holes penetrate through the aiming plate top surface and the aiming plate bottom surface and are located between the aiming holes, the fixed part is provided with a plurality of threading openings at the position corresponding to the threading holes, the threading openings penetrate through the fixed part top surface and the fixed part bottom surface of the fixed part; when the fixed part is placed on the acromioclavicular joint and the aiming holes overlap with the matching holes of the fixed part, the threading openings of the fixed part overlap with the threading holes of the aiming plate.

8. The bone plate according to claim 7, wherein an arrangement direction of the threading holes on the aiming plate is not parallel to an arrangement direction of the aiming holes on the aiming plate.

* * * * *